| United States Patent [19] | [11] Patent Number: 4,992,598 |
| --- | --- |
| Strutz et al. | [45] Date of Patent: Feb. 12, 1991 |

[54] PURIFICATION OF 1, 1, 1-TRIS(4'-HYDROXYPHENYL)ETHANE

[75] Inventors: Heinz Strutz, Frankfurt, Fed. Rep. of Germany; Werner Mueller, Corpus Christi, Tex.

[73] Assignee: Hoechst Celanese Corporation, Somerville, N.J.

[21] Appl. No.: 478,072

[22] Filed: Feb. 9, 1990

[51] Int. Cl.$^5$ .............................................. C07C 39/12
[52] U.S. Cl. ...................................... 568/720; 568/756
[58] Field of Search .................... 568/720, 724, 756; 552/115

[56] References Cited

U.S. PATENT DOCUMENTS

| 2,789,143 | 4/1957 | Arnold et al. | 568/756 |
| 3,544,514 | 12/1970 | Schnell | 260/7 |
| 3,579,542 | 5/1971 | Meyer et al. | 260/395 |
| 3,644,538 | 2/1972 | Starnes | 568/720 |
| 3,969,421 | 7/1976 | d'Ostrowick et al. | 568/756 |
| 4,337,369 | 6/1982 | Vanderpool et al. | 568/756 |
| 4,385,191 | 5/1983 | Petrille et al. | 568/756 |
| 4,394,496 | 7/1983 | Schrader | 528/98 |

Primary Examiner—Richard L. Raymond
Assistant Examiner—Raymond Covington
Attorney, Agent, or Firm—Richard S. Roberts; Shirley L. Church

[57] ABSTRACT

A process for the purificationof 1,1,1-tris(4'-hydroxyphenyl)ethane by washing a crude admixture containing both it and impurities with a saturated solution of 1,1,1-tris(4'-hydroxyphenyl)ethane in water and methanol; and isolating the washed crude admixture from the effluent and dissolving the washed crude admixture in methanol, and adding water and sodium borohydride to the dissolved, washed crude admixture to form a precipitate of 1,1,1-tris(4'-hydroxyphenyl)ethane, and filtering the precipitate to form a resultant purified 1,1,1-tris(4'-hydroxyphenyl)ethane and a filtrate. Another embodiment of the invention provides iteratively repeating the process by washing an additional crude admixture batch with the filtrate from a prior purification.

20 Claims, No Drawings

PURIFICATION OF 1,1,1-TRIS(4'-HYDROXYPHENYL)ETHANE

BACKGROUND OF THE INVENTION

The present invention relates to the production of 1,1,1-tris(4'-hydroxyphenyl)ethane (THPE) or more particularly to a method of purifying 1,1,1-tris(4'-hydroxyphenyl)ethane. It is known in the art that 1,1,1-tris(4'-hydroxyphenyl)ethane may be produced by reacting 4-hydroxyacetophenone with phenol. Typically this is performed with phenol also used as the solvent for the mixture. The reaction proceeds under acidic catalytic conditions such as a co-catalyst system of hydrochloric acid and beta-mercaptopropionic acid. A problem with this reaction is that the yield is relatively low, i.e. only about 70-80% and the product contains substantial amounts of impurities. These include iso-THPE which is a mixture of ortho- and para-tris(hydroxyphenyl)ethane isomers, 1,1-bis(hydroxyphenyl)ethene isomers, phenol, 4-hydroxyacetophenone, chloride, as well as unidentified color bodies and light and heavy ends. Although pure THPE is white, the reaction product is a reddish-brown mixture of pure and impure product. THPE is used as a hardener for epoxies and as a crosslinker for polycarbonates. As such, its color must be white. The present invention provides a purification process which uses only a single recrystallization from methanol/water. It has been found that white and very pure THPE will be obtained if the crude reaction mixture is washed with a THPE saturated wash/methanol liquid prior to the single recrystallization or more preferably with the wash filtrate liquid of a preceding recrystallization although this is colored and rich in the above mentioned impurities. It has been found that by use of such a wash yields of pure and white THPE are good, and solvents have a more productive use. On the other hand only a single recrystallization is necessary if the crude THPE is initially washed with the filtrate from a preceding recrystallization.

The results of the filtrate wash and the following single recrystallization are dependent on the phenol content prior to the wash. By washing the highly colored crude THPE with filtrate from a prior THPE recrystallization, phenol can be removed from the crude cake almost quantitatively. Although the filtrate is saturated with THPE, the recovery of THPE is not quantitative due to the dissolving effect of phenol during the initial wash. A higher recovery is observed for a crude admixture with a lower phenol content. In general lower phenol content raises THPE recovery, however, if phenol content is too low, impurities are not removed satisfactorily. A crude admixture having a phenol content of about 5% maximized recovery of exceedingly pure THPE.

As a result of the process, most of the color bodies are removed in the wash stage where the color of the crude THPE changes from a dark rusty color to a light tan. The balance is removed in the recrystallization. Best results are obtained when the recrystallization filtrate has a water content which has been adjusted to between 60 and 75%. The use of a higher amount of water gives higher THPE recoveries, but the material fails to meet the white color requirement in the following single recrystallization.

For the crude THPE washed with recycled recrystallization filtrate, only a single recrystallization from methanol/water is necessary to meet the white color and high purity requirements. This recrystallization is basically a precipitation of THPE from the methanol/water solution. The simplicity of this purification procedure was very unexpected with respect to the complexity of the crude mixture and the close similarity of some components of the crude mixture. Thus, this procedure is substantially low in labor and capital costs. In another embodiment of the invention, if a partial phenol removal from the crude reaction product is performed prior to the wash, the process has some increased costs compared to the simple wash/single recrystallization process, but there is a substantially higher refining recovery. In either case, waste management is simplified because phenol and chloride containing waste water streams from hot water washes are avoided, and the other waste streams can be substantially minimized.

SUMMARY OF THE INVENTION

The invention provides a process for the purification of 1,1,1-tris(4'-hydroxyphenyl)ethane from a substantially solid crude admixture containing 1,1,1-tris(4'-hydroxyphenyl)ethane and impurities resulting from the catalytic production of 1,1,1-tris(4'-hydroxyphenyl)ethane from 4-hydroxyacetophenone and phenol, the process comprising:

(a) washing said crude admixture with a saturated solution of 1,1,1-tris(4'-hydroxyphenyl)ethane in a solute comprising from about 60% to about 75% by weight of water and from about 25% to about 40% by weight of methanol; and (b) isolating the thusly washed crude admixture from the formed effluent washing composition, and dissolving said washed crude admixture in methanol, and (c) adding sufficient water and sodium borohydride to said dissolved, washed crude admixture to form a precipitate of 1,1,1-tris(4'-hydroxyphenyl)ethane, and (d) filtering said precipitate to thereby form a purified 1,1,1-tris(4'-hydroxyphenyl)ethane and a filtrate; and (e) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate.

The invention also provides an iterative purification process for the purification of 1,1,1-tris(4'-hydroxyphenyl)ethane from a substantially solid crude admixture containing 1,1,1-tris(4'-hydroxyphenyl)ethane and impurities resulting from the catalytic production of 1,1,1-tris(4'-hydroxyphenyl)ethane from 4-hydroxyacetophenone and phenol, the process comprising:

(a) washing said crude admixture with a saturated solution of 1,1,1-tris(4'-hydroxyphenyl)ethane in a solute comprising from about 60% to about 75% by weight of water and from about 25% to about 40% by weight of methanol; and (b) isolating the thusly washed crude admixture from the formed effluent washing composition, and dissolving said washed crude admixture in methanol, and (c) adding sufficient water and sodium borohydride to said dissolved, washed crude admixture to form a precipitate of 1,1,1-tris(4'-hydroxyphenyl)ethane, and (d) filtering said precipitate to thereby form a purified 1,1,1-tris(4'-hydroxyphenyl)ethane and a filtrate; and (e) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate; and (f) washing an additional crude admixture with the filtrate from step (d) optionally combined with the rinse effluent from step (e), and (g) isolating the thusly washed crude admixture from the formed effluent washing composition, and dissolving said washed crude admixture in methanol, and (h) adding sufficient water and sodium borohydride to said dissolved, washed additional crude admixture to form an additional precipitate of 1,1,1-tris(4'-hydroxyphenyl)ethane, and (i) filtering said additional precipitate to thereby form a purified 1,1,1-tris(4'-hydroxyphenyl)ethane and another filtrate; and (j) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate.

The process may further comprise repeating steps (f) through (h) at least once wherein the filtrate from step (i) optionally combined with the rinse effluent from step (j) is used in the washing of step (f).

In another embodiment of the invention, prior to step (a) above, and/or between steps (e) and (f), the phenol content of the crude admixture is adjusted to an amount of from 1% to about 30% based on the weight of the crude admixture.

DETAILED DESCRIPTION OF THE PREFERRED EMBODIMENT

As hereinbefore mentioned, the production of 1,1,1-tris(4'-hydroxyphenyl)ethane may be performed by the reaction of 4-hydroxyacetophenone with phenol, wherein phenol is the supporting solvent as well as a reagent. The reaction takes place under catalytic conditions, with hydrochloric acid and beta-mercaptopropionic acid as preferred co-catalyst. The resulting reaction product contains significant amounts of impurities which are removed by the method of this invention. The impure, substantially solid crude admixture contains 1,1,1-tris(4'-hydroxyphenyl)ethane (THPE), residual 4-hydroxyacetophenone, phenol, chlorides, THPE isomers, bis-(hydroxyphenyl)ethene isomers, color bodies and other unidentified parts which are sought to be removed.

In the first step of the purification method, one washes the crude admixture with a saturated solution of 1,1,1-tris(4'-hydroxyphenyl)ethane in a solute comprising from about 60% to about 75% by weight of water and from about 25% to about 40% by weight of methanol. Preferably this washing is conducted in several washing steps. It has been found that by employing a saturated solution of THPE in the washing solution, that THPE loss from the crude admixture is substantially reduced. Prior to washing, the crude admixture typically contains from about 15% to about 30% by weight of residual phenol. Since phenol is a good solvent for THPE, it is desired to reduce the phenol content prior to the washing step simply by vacuum draw of the phenol. However, it has been found that if too much phenol is drawn off, that although the THPE recovery is good, the purity of the product is unsatisfactory. Loss of THPE during the wash of the crude admixture is basically caused by the presence of phenol although the washing solution is THPE saturated. Phenol content may be controlled by pumping off the crude admixture before the wash or by use of a hot nitrogen flow through the crude admixture to cause the phenol, which is the most volatile component, to leave the system before the wash. Generally it is desired to obtain THPE with a 99.5% or greater purity and having a whiteness measure (APHA) of 200 or less, preferably 150 or less. Therefore a phenol content of at least about 1.0% and up to about 30.0% based on the weight of the crude admixture is desired. More preferably the phenol content is adjusted to from about 4.0% to about 10% and most preferably from about 4.5% to about 7.5%. A single most preferred phenol content is about 5.0%. Therefore, in the most preferred case, the phenol content of the crude admixture is first adjusted to these levels before conducting the washing step.

Next, after the washing step, one isolates the washed crude admixture from the formed effluent washing composition. This can be done by performing the washing on a filter plate while stirring and then drawing down the filtrate. The solid, washed crude admixture is then dissolved in sufficient methanol to effect a dissolution.

One then adds sufficient water and sodium borohydride to reduce the dissolved, washed crude admixture and to form a precipitate of 1,1,1-tris(4'-hydroxyphenyl)ethane. The sodium borohydride also acts as a pH adjusting reagent during the recrystallization. In the preferred embodiment, the amount of sodium borohydride added ranges from about 0.0003% to about 0.3%, preferably from about 0.003% to about 0.07% and most preferably from about 0.01% to about 0.03% based on the weight of methanol and water. If the phenol content in the crude admixture has been reduced prior to washing, it is preferred that sodium borohydride is added to the methanolic solution THPE solution. After stirring, carbon in the form of charcoal, is added to the methanolic THPE solution and filtered off prior to having added more sodium borohydride plus water. This is most advantageous when the phenol content has been reduced to 15% or less in the pre-washed crude admixture. In the preferred embodiment, the amount of carbon added ranges from about 0.001% to about 1.0%, preferably from about 0.01% to about 0.8%, and most preferably from about 0.05% to about 0.3% based on the weight of methanol.

One then filters the precipitate to thereby form a purified, recrystallized 1,1,1-tris(4'-hydroxyphenyl)ethane and a filtrate. The next step is rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate. The rinse mixture preferably comprises water and methanol in a 2:1 to 6:1 weight ratio. One may perform an optional stabilizing rinse with an aqueous sodium dithionate solution at this stage. Typical sodium dithionate solutions may range from about 0.01% to about 1.0%, preferably from about 0.05% to about 0.5% by weight in water. Finally, the product is dried.

In one key embodiment of the invention, it has been unexpected found that one may use this colored, resultant filtrate as the washing solution in the washing step of another crude admixture batch. Although this filtrate contains sodium borohydride and removed, colored bodies and other impurities in addition to water, methanol and THPE, it has been found that these are substantially removed in the effluent of the washing step. If the filtrate color is pink one should treat it with sodium dithionate to change it to a light yellow color prior to using the filtrate to wash the next batch of crude admixture. A suitable amount is about 0.1 weight percent of saturated aqueous sodium dithionate. Therefore, this filtrate serves double duty in the overall process and significantly reduces the amount of fluids which must be recycled or treated before ultimate discharge.

The following non-limiting examples serve to illustrate the invention.

EXAMPLES 1-5

Purification of Crude THPE Without a Preceding Phenol Removal Wash of Crude THPE Under $N_2$ (glove bag) crude THPE is washed in portions in a filter funnel with filtrate from a prior recrystallization after the water content is adjusted. Before the wash filtrate is sucked down, the slurry is intensively stirred. The last filtrate shows only a very slight pink color. The residue is dried overnight at 40° C./125 mmHg to yield a tan to slightly orange product. The results appear in Table I.

EXAMPLES 6-11

Recrystallization of Washed THPE

Under $N_2$ (glove bag), washed crude THPE is dissolved in methanol to give a dark amber solution. After the addition of sodium borohydride, the solution first turns colorless and then a light orange-amber. After stirring for 0.5 hrs, water dosed with $NaBH_4$ (slight gas evolution) is added during a 1 hour period while stirring. The slurry is filtered, the residue washed twice with a THPE saturated water/methanol mixture (5.1:1) and then dried overnight (40° C., 125 mmHg) to yield purified THPE. The results are summarized in Table II.

EXAMPLES 12-17

Purification of Crude THPE Having a Low Phenol Content Removal of Phenol from Crude THPE Crude THPE is placed on the filter plate of a filter funnel (d=1.5',h=5') which is connected to a $N_2$ fine valve at the bottom and to a receiver flask at the top. The funnel, including the connection joint to the receiver flask, is heated to 55° C. and the receiver flask is cooled in a dry ice/acetone bath. A vacuum of 30 to 35 mmHg is maintained by a high vacuum pump connected to the receiver flask and controlled by a slight $N_2$ stream through the bottom of the filter funnel and the THPE cake. After 5 hours no additional phenol sublimes. The cake, which appears to be brighter in color, is cooled down to room temperature under $N_2$ and then transferred to a glove bag for the filtrate wash. Results are summarized in Table III.

EXAMPLES 18-28

Filtrate Wash of Phenol Reduced Crude THPE

Under $N_2$ (glove bag) crude THPE is intensively mixed with phenol to increase the phenol content. This mixture is washed in portions in a filter funnel with filtrate from a prior recrystallization (water content after adjustment: See Table IV). Before the washing filtrate is sucked down, the slurry is stirred vigorously. The last filtrate shows only a very light pink color. The cake is dried overnight at 40° C./125 mmHg to yield a tan to light pink product. The filtrate from the single recrystallization procedure can especially be successfully used if it is previously treated with sodium dithionate (ca. 0.7 ml of a saturated aqueous solution per 619 g of filtrate) to change the color from pink to light yellow. The results are reported in Table IV.

Examples 29-34

Single Recrystallization of Crude THPE Low in Phenol Content

Under $N_2$ (glove bag), washed crude THPE is dissolved in 37.2 g methanol to give a green-amber solution. After the addition of 20 mg sodium borohydride, causing a color change to orange-amber, the solution is stirred for 30 minutes and then treated with 100 mg carbon for 1 hr. The carbon is filtered off using Celite as a filter aid. The carbon/Celite cake is rinsed with 31.7 g methanol. The combined filtrates are treated with another 9 mg $NaBH_4$ and stirred for 15 min. Finally, 140 g of water dosed with 12 mg $NaBH_4$ (slight gas evolution)—are added over 1 hour. The slurry is filtered, residue washed twice with a THPE saturated water/methanol mixture 5.1:1, 85.4 g total) and dried overnight at 40° C./125 mmHg to yield purified THPE. The results are summarized in Table V.

TABLE I

| | | | | WASH OF CRUDE THPE | | | | | |
|---|---|---|---|---|---|---|---|---|---|
| Ex. | W (g) | [1]THPE Wt % | [2]Phenol Wt % | [3]$H_2O$ Wt % | [4]F/THPE | [5]THPE % | [6]THPE wt % | [7]Phenol wt % | [8]Cl ppm |
| 1 | 80.4 | 75.3 | 23.2 | 63 | 9.0 | 84.4 | 97.8 | 0.65 | 70 |
| 2 | 80.7 | 75.3 | 23.2 | 63 | 5.3 | 81.4 | 96.0 | 0.65 | 40 |
| 3 | 29.8 | 75.3 | 23.2 | 63 | 5.5 | 83.3 | 98.2 | 0.52 | <1 |
| 4 | 273.2 | 75.3 | 23.2 | 67.1 | 5.4 | 82.7 | 96.9 | 0.67 | 79 |
| 5 | 296.0 | 73.1 | 19.7 | 64.8 | 5.4 | 92.1 | 97.2 | 0.73 | 30 |

W: Weight of crude starting material;
[1]THPE: THPE content in starting material;
[2]Phenol: Phenol content in starting material;
[3]$H_2O$: Water content in filtrate;
[4]F/THPE: Weight ratio of filtrate to starting material;
[5]THPE: THPE recovery based on content in crude material
[6]THPE: Purity of THPE in washed material;
[7]Phenol: Phenol content in washed material;
[8]Cl: Chloride content in washed material;

TABLE II

SINGLE RECRYSTALLIZATION OF WASHED CRUDE THPE +

| Example No. | Washed THPE from Example | ¹THPE g | ²THPE wt-% | ³Rinse/ THPE | ⁴THPE wt-% | ⁵THPE % | APHA |
|---|---|---|---|---|---|---|---|
| 6. | 4 | 20.05 | 96.9 | 1.3 ++ | 99.5 | 98.6 | 115 |
| 7. | 4 | 20.07 | 96.9 | 2.8 | 99.5 | 98.2 | 105 |
| 8. | 4 | 20.02 | 96.9 | 2.9 | 99.6 | 98.0 | 145 |
| 9. | 5 | 20.38 | 97.2 | 3.4 | 99.8 | 97.5 | 120 |
| 10. | 5 | 20.33 | 97.2 | 2.9 | 99.6 | 99.0 | 120 |
| 11.* | 5 | 20.08 | 97.2 | 3.5 | 99.7 | 98.9 | 140 |

¹weight of washed crude THPE;
²THPE: THPE content in crude THPE;
³Rinse/THPE: Weight ratio of rinse solution ($H_2O:CH_3OH$ = 5.1, THPE saturated) to crude THPE;
⁴THPE: purity of recrystallized THPE;
⁵THPE: recovery of THPE in recrystallization, based on THPE;
APHA: color number;
+ from 36.8 g methanol, 20 mg $NaBH_4$/98 g water, 12 mg $NaBH_4$
++ sodium dithionate wash after rinse (70 g, 0.14 wt % $Na_2S_2O_4$);
*only 6 mg $NaBH_4$ in 98 g water;

TABLE III

REMOVAL OF PHENOL FROM CRUDE THPE IN A FILTER FUNNEL

| Example No. | W g | ¹Phenol wt % | ²Funnel inch | ³Prod. g | ⁴Phenol wt % |
|---|---|---|---|---|---|
| 12 | 46.5 | 27.2 | 1.5 | 32.4 | 1.4 |
| 13 | 111.0 | 29.2 | 1.5 | | 1.2 |
| 14 | 101.0 | 27.2 | 1.5 | 69.5 | 1.1 |
| 15 | 103.0 | 28.5 | 1.5 | 71.05 | 1.2 |
| 16 | 116.0 | 27.2 | 1.5 | 80.9 | 0.9 |
| 17 | 215 | 28.2 | 3.1 | 152.2 | 3.9 |

W: weight of starting material;
¹Phenol: phenol content in starting material;
²Funnel: diameter of filter funnel;
³Prod.: weight of crude THPE after phenol removal;
⁴Phenol: phenol content in crude THPE after phenol removal;
Conditions: 55° C., 30–35 mmHg, permanent $N_2$ sparge through filter plate.

TABLE IV

FILTRATE WASH OF PHENOL REDUCED CRUDE THPE

| Ex. No. | W g | ¹THPE wt-% | ²Phenol wt-% | ³H₂O wt-% | ⁴F/THPE | ⁵THPE % | ⁶THPE wt-% | ⁷PHENOL wt-% |
|---|---|---|---|---|---|---|---|---|
| 18 | 296.0 | 73.1 | 19.7 | 64.8 | 5.4 | 92.1 | 97.2 | 0.73 |
| 19 | 59.93 | 88.5 | 5.1 | 66.3 | 9.1 | 98.3 | 97.1 | 0.41 |
| 20 | 32.65 | 89.7 | 7.5 | 65.8 | 6.4 | 95.9 | 98.3 | not anal. |
| 21 | 32.08 | 91.9 | 7.5 | 66,6 | 7.0 | 94.5 | 99.1 | 0.48 |
| 22 | 32.97 | 89.4 | 10.0 | 66.0 | 6.9 | 93.1 | 99.2 | not anal. |
| 23 | 65.07 | 92.2 | 5.0 | 65.8 | 9.6 | 96.3 | 98.6 | 0.40 |
| 24 | 76.39 | 91.6 | 5.0 | 67.5 | 10.2 | 95.2 | 98.2 | 0.46 |
| 25 | 53.35 | 91.6 | 5.2 | 63.8 | 9.8 | 94.8 | 97.0 | 0.49 |
| 26 | 53.36 | 91.2 | 5.0 | 63.8 | 9.6 | 97.2 | 98.4 | 0.47 |
| 27 | 38.57 | 91.6 | 5.0 | 64.7 | 9.6 | 96.5 | 98.4 | 0.43 |
| 28* | 63.95 | 91.0 | 5.0 | 64.7 | 9.7 | 94.2 | 97.7 | 0,43 |

For footnote explanations: see Table 1.
Filtrates from preceding single recrystallizations
*Filtrate from preceding single recrystallization, treated with ca. 0.7 g of saturated aqueous $Na_2S_2O_4$

TABLE V

SINGLE CRYSTALLIZATION OF REDUCED THPE AFTER PHENOL STRIP AND FILTRATE WASH +

| Example No. | Washed THPE from example | ¹THPE g | ²THPE wt-% | ³RINSE/THPE | ⁴THPE wt-% | ⁵THPE % | APHA |
|---|---|---|---|---|---|---|---|
| 29 | 25 | 20.14 | 97.0 | 4.4 | 99.6 | 95.4 | 100 |
| 30 | 25 | 20.13 | 97.0 | 3.9 | 99.6 | 97.7 | 130 |
| 31 | 26 | 20.07 | 99.4 | 4.2 | 99.7 | 95.0 | 133 |
| 32 | 26 | 20.04 | 99.4 | 4.2 | 99.6 | 94.7 | 123 |
| 33 | 28 | 20.27 | 97.7 | 4.6 | 99.7 | 95.9 | 80 |
| 34 | 28 | 20.14 | 97.7 | 4.4 | 99.7 | 95.4 | 120 |

For footnote explanations: see Table II
+ from 68.9 g MeOH, 0.029 g $NaBH_4$, 0.1 g carbon/140 g $H_2O$, 0.012 g $NaBH_4$

What is claimed is:

1. A process for the purification of 1,1,1-tris(4'-hydroxyphenyl)ethane from a substantially solid crude admixture containing 1,1,1-tris(4'-hydroxyphenyl)ethane and impurities resulting from the catalytic production of 1,1,1-tris(4'-hydroxyphenyl)ethane from 4-hydroxyacetophenone and phenol, the process comprising:

(a) washing said crude admixture with a saturated solution of 1,1,1-tris(4'-hydroxyphenyl)ethane in a solute comprising from about 60 to about 75% by weight of water and from about 25% to about 40% by weight of methanol; and (b) isolating the thusly washed crude admixture from the formed effluent washing composition, and dissolving said washed crude admixture in methanol, and (c) adding sufficient water and sodium borohydride to said dissolved, washed crude admixture to form a precipitate of 1,1,1-tris(-4'-hydroxyphenyl)ethane, and (d) filtering said precipitate to thereby form a purified 1,1,1-tris(-4'-hydroxyphenyl)ethane and a filtrate; and (e) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate.

2. The process of claim 1 wherein the crude admixture of step (a) has a phenol content of from about 4.0% to about 27.0% by weight of the admixture.

3. The process of claim 1 wherein the crude admixture of step (a) has a phenol content of from about 4.0% to about 15.0% by weight of the admixture.

4. The process of claim 1 wherein the crude admixture of step (a) has a phenol content of from about 4.5% to about 7.0% by weight of the admixture.

5. The process of claim 1 wherein first sodium borohydride and then carbon are additionally added to the crude washed admixture dissolved in methanol after step (b) and then the carbon filtered off prior to step (c).

6. The process of claim 1 further comprising the subsequent step of rinsing the filtered precipitate with an aqueous solution of sodium dithionate.

7. A process for the purification of 1,1,1-tris(4'-hydroxyphenyl)ethane from a substantially solid crude admixture containing 1,1,1-tris(4'-hydroxyphenyl)ethane and impurities resulting from the catalytic production of 1,1,1-tris(4'-hydroxyphenyl)ethane from 4-hydroxyacetophenone and phenol, the process comprising:

(a) washing said crude admixture with a saturated solution of 1,1,1-tris(4'-hydroxyphenyl)ethane in a solute comprising from about 60% to about 75% by weight of water and from about 25% to about 40% by weight of methanol; and (b) isolating the thusly washed crude admixture from the formed effluent washing composition, and dissolving said washed crude admixture in methanol, and (c) adding sufficient water and sodium borohydride to said dissolved, washed crude admixture to form a precipitate of 1,1,1-tris(4'-hydroxyphenyl)ethane, and (d) filtering said precipitate to thereby form a purified 1,1,1-tris(4'-hydroxyphenyl)ethane and a filtrate, and (e) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate, and (f) washing an additional crude admixture with the filtrate from step (d) optionally combined with the rinse effluent from step (e), and (g) isolating the thusly washed crude admixture from the formed effluent washing composition, and dissolving said washed crude admixture in methanol, and (h) adding sufficient water and sodium borohydride to said dissolved, washed additional crude admixture to form an additional precipitate of 1,1,1-tris(4'-hydroxyphenyl)ethane, and (i) filtering said additional precipitate to thereby form a purified 1,1,1-tris(4'-hydroxyphenyl)ethane and another filtrate; and (j) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate.

8. The process of claim 7 wherein the crude admixture of step (a) has a phenol content of from about 4.0% to about 27.0% by weight of the admixture.

9. The process of claim 7 wherein the crude admixture of step (a) has a phenol content of from about 4.0% to about 15.0% by weight of the admixture.

10. The process of claim 7 wherein the crude admixture of step (a) has a phenol content of from about 4.5% to about 7.0% by weight of the admixture.

11. The process of claim 7 further comprising repeating steps (f) through (j) at least once wherein the filtrate from step (i) optionally combined with the rinse effluent from step (j) is used in the washing of step (f).

12. The process of claim 7 wherein first sodium borohydride and then carbon are additionally added to the crude washed admixture dissolved in methanol after steps (b) and (g) and then the carbon filtered off prior to steps (c) and (h).

13. The process of claim 7 further comprising the subsequent step of rinsing the filtered precipitate with an aqueous solution of sodium dithionate.

14. In a process for the purification of 1,1,1-tris(4'-hydroxyphenyl)ethane from a substantially solid crude admixture containing 1,1,1-tris(4'-hydroxyphenyl)ethane and impurities resulting from the catalytic production of 1,1,1-tris(4'-hydroxyphenyl)ethane from 4-hydroxyacetophenone and phenol, in which a filtrate has been formed by:

(a) washing said crude admixture with a saturated solution of 1,1,1-tris(4'-hydroxyphenyl)ethane in a solute comprising from about 60% to about 75% by weight of water and from about 25% to about 40% by weight of methanol; and (b) isolating the thusly washed crude admixture from the formed effluent washing composition, and dissolving said washed crude admixture in methanol, and (c) adding sufficient water and sodium borohydride to said dissolved, washed crude admixture to form a precipitate of 1,1,1-tris(4'-hydroxyphenyl)ethane, and (d) filtering said precipitate to thereby form a purified 1,1,1-tris(4'-hydroxyphenyl)ethane and a filtrate, and (e) rinsing the resultant filtered precipitate of 1,1,1-tris( 4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate the process comprising:

(i) washing an additional crude admixture with the filtrate from step (d) optionally combined with the rinse effluent from step (e), and (ii) isolating the thusly washed crude admixture from the formed effluent washing composition, and dissolving said washed crude admixture in methanol, and (iii) adding sufficient water and sodium borohydride to said dissolved, washed additional crude admixture to form an additional precipitate of 1,1,1-tris(4'-hydroxyphenyl)ethane, and (iv) filtering said additional precipitate to thereby form a purified 1,1,1-tris(4'-hydroxyphenyl)ethane and another filtrate; and (v) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate.

15. The process of claim 14 wherein the crude admixture of steps (a) and (i) have a phenol content of from about 4.0% to about 27.0% by weight of the admixture.

16. The process of claim 14 wherein the crude admixture of steps (a) and (i) have a phenol content of from about 4.0% to about 15.0% by weight of the admixture.

17. The process of claim 14 wherein the crude admixture of steps (a) and (i) have a phenol content of from about 4.5% to about 7.0% by weight of the admixture.

18. The process of claim 14 wherein steps (i) through (v) are repeated at least once wherein the filtrate from step (iv) optionally combined with the rinse effluent from step (v) is used in the washing of step (i).

19. The process of claim 14 wherein first sodium borohydride and then carbon are additionally added to the crude washed admixture dissolved in methanol after steps (b) and (ii) and then the carbon filtered off prior to steps (c) and (iii).

20. The process of claim 14 further comprising the subsequent step of rinsing the filtered precipitate from steps (d) and (iv) with an aqueous solution of sodium dithionate.

* * * * *